United States Patent [19]

Speelman

[11] Patent Number: 4,505,274
[45] Date of Patent: Mar. 19, 1985

[54] SUTURE CLIP

[75] Inventor: Irving A. Speelman, East Williston, N.Y.

[73] Assignee: Propper Manufacturing Co., Inc., Long Island City, N.Y.

[21] Appl. No.: 433,685

[22] Filed: Oct. 12, 1982

Related U.S. Application Data

[63] Continuation of Ser. No. 198,194, Oct. 17, 1980, abandoned.

[51] Int. Cl.³ .............................................. A61B 17/08
[52] U.S. Cl. .................................................... 128/337
[58] Field of Search ................... 128/337, 335, 334 R, 128/346, 321, 325; 227/DIG. 1; 24/259 R, 560, 565, 513; 411/462, 463, 464, 465

[56] References Cited

U.S. PATENT DOCUMENTS

| | | | |
|---|---|---|---|
| 733,723 | 7/1903 | Lukens. | |
| 2,201,610 | 5/1940 | Dawson, Jr. | 128/337 |
| 2,232,142 | 2/1941 | Schumann | 128/335 |
| 2,254,620 | 9/1941 | Miller | 128/337 |
| 2,317,815 | 4/1943 | Schumann | 1/56 |
| 2,684,070 | 7/1954 | Kelsey | 128/337 |
| 2,811,971 | 11/1957 | Scott | 128/335 |
| 3,068,870 | 12/1962 | Levin | 128/337 |
| 3,586,002 | 6/1971 | Wood | 128/337 |
| 4,212,305 | 7/1980 | Lahay | 128/321 X |
| 4,337,774 | 7/1982 | Perlin | 128/346 X |

FOREIGN PATENT DOCUMENTS 293301 10/1928 United Kingdom ................ 128/337

OTHER PUBLICATIONS

Data Sheet Showing Wachenfeldt Suture Clip.
Sample of "Wachenfeldt Suture Clip" Which is Commercially Available from Jetter & Scheerer Corp.

Primary Examiner—Michael H. Thaler

[57] ABSTRACT

A one-piece suture clip, for holding the edges of a wound together, is constructed from a continuous metal strip formed into a pair of coacting arms adjacent a central bending region. Each arm includes a sharp projection for grasping the skin adjacent the wound and a pair of reinforced tabs. The tabs are rigidly secured to a common lower member of the arms to permit opening of the arms from the clamping position for removal of the suture clip.

3 Claims, 4 Drawing Figures

SUTURE CLIP

This is a continuation of application Ser. No. 198,194, filed Oct. 17, 1980, now abandoned.

DESCRIPTION OF THE INVENTION

This invention relates in general to suture clips, and more particularly, to suture clips constructed of a one-piece design which readily permits the opening of the suture clip from a clamping position for removal.

Suture clips are clamping devices used to close and retain the opposite skin edges of a wound or incision in extremely close approximation for healing by applying a force directly to the juxtaposed skin edges. The suture clip is designed to replace the conventional threaded stitch with its associated painful insertion. Suture clips have been generally found to be capable of being applied more rapidly than the conventional threaded stitch, will hold the marginal edges of wounds or incisions in closer approximation thereby developing less scar tissue upon healing, and are more easily removed from the body tissue after the healing than the threaded stitch.

A suture clip of three-piece construction is disclosed in U.S. Pat. No. 2,232,142. The suture clip includes a main body having projecting prongs at either end and constructed of relatively soft material so as to be easily bent by the operating surgeon. Two identical reinforcing members of relatively hard material are disposed onto the main body and clamped thereabout. The reinforcing members include tabs which extend outward and which are equally spaced from the ends of the main body. As the suture clip is bent into a clamping position, the main body bends about its center due to its construction from relatively soft material. The tabs assume a substantially V-shaped relationship with the prongs enter the skin adjacent the wound such that the suture clip maintains the edges of the wound in close approximation. Thereafter, the squeezing of the tabs together unbends the main body due to the tabs construction from relatively hard material and retracts the prongs from the skin.

The above-described prior art suture clip required a three-piece construction, using relatively hard material for the two reinforcing members including the tabs, and a softer material for the main body to allow the main body of the suture clip to be bent during use and unbent during removal. Further, the three-piece construction requires the fabrication and assembling of three separate clip components along with their associated increased costs for fabrication, quality control, and inspection.

There is also known in the prior art, a one-piece suture clip, sold under the trademark Wachenfeldt. However, in order for the tabs to have sufficient mechanical strength to be used for unbending the prior art suture clip, the entire clip is constructed from relatively hard material and of relatively thick cross-section. Since the material is relatively hard and of relatively thick cross-section, the normal variations due to tolerance may result in signficiant differences in force required to bend the suture clips from different lots, thereby making such prior art one-piece suture clips less desirable.

It is broadly an object of the present invention to provide a suture clip of one-piece construction which overcomes or avoids one or more of the foregoing disadvantages of conventional suture clips by providing a suture clip of one-piece construction that can be easily bent into a clamping position and subsequently opened for removal.

A further object of the present invention is to provide a suture clip of one-piece construction of relatively thin gauge material that has sufficiently rigid tabs to allow for the unbending of the suture clip for removal.

A still further object of the present invention is to provide a suture clip of one-piece construction which requires an applying force that is substantially uniform from one clip to another.

In accordance with one embodiment of the present invention, there is provided a suture clip for holding the edges of a wound proximate to one another. The suture clip is constructed from a metal strip formed to include an arched body portion having a central bending region and a pair of projecting prongs at opposite ends of the arched body portion. Those portions of the metal strip which extend beyond the arched body portion are bent back over the arched body portion in overlying relationship and are secured to the arched body portion adjacent the central bending region. The ends of the metal strip extend away from said arched body portion adjacent the central bending region to form a pair of outwardly extending tabs. Reinforcing webs engage the tabs and the overlying portion to establish the angular position of the tabs with respect to the overlying portion to permit the opening of the suture clip by applying pressure to the tabs for removing the suture clip from a wound.

Further, in accordance with the above embodiment, the body of the suture clip is formed from a continuous metal strip and wherein the reinforcing webs are formed as a protruding part of the metal strip overlying an area of the bending portion.

The above brief description as well as further objects, features, and advantages of the present invention will be more fully understood by reference to the following detailed description of a presently preferred but nonetheless illustrative suture clip in accordance with the present invention when taken in conjunction with the accompanying drawings, wherein.

Figure 1:
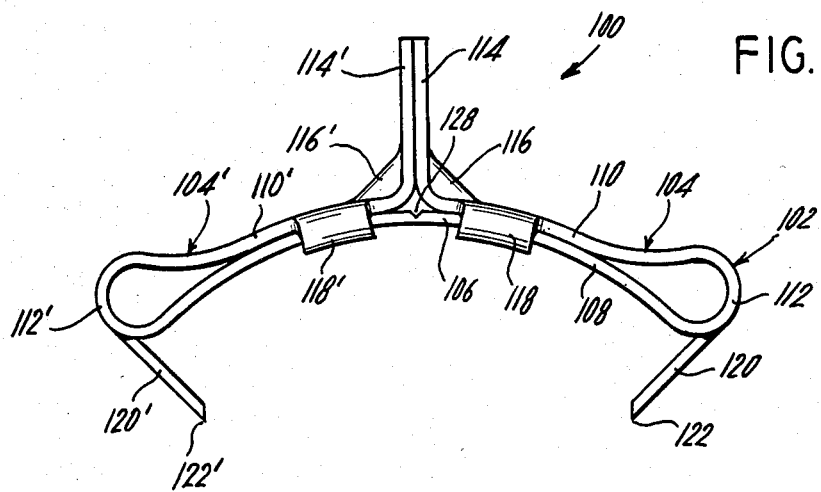
FIG. 1 is a side elevation of a one-piece suture clip constructed from a body to include a central bending portion and a pair of coacting arms joined by the bending portion, skin-piercing prongs projecting downward at one end of each arm, and tabs extending outward at the other end of each arm.

Referring to the drawings generally, there is illustrated a one-piece suture clip 100 for holding the edges of a wound or incision in accurate approximation to one another. The suture clip 100 is fabricated from a metal strip having uniform tensile strength or hardness. Alloy compositions which have been found acceptable for the metal strip are, for example, an alloy which has a composition of about 65% copper, 18% nickel, and 17% zinc; and an alloy which has a composition of about 60% copper, 18% nickel and 22% zinc.

Referring specifically to FIG. 1, the suture clip 100 is constructed from a continuous metal strip into a one-piece slightly arched body 102. The body 102 includes a pair of coacting arms 104, 104' joined by a central bending portion 106. The arms 104, 104' include a common lower strip 108, which includes the central bending portion or region 106, and upper strips 110, 110'. The upper strips 110, 110' are bent over the lower strip 108 in overlying relationship in a manner to form loops 112, 112' at the ends of the arms 104, 104'. Overlying the central bending portion 106, and formed from the free end of the upper strips 110, 110', are outwardly extending tabs 114, 114' arranged to be in generally abutting relationship. The tabs 114, 114' include reinforcing webs 116, 116' formed between the tabs and the upper strips 110, 110', and overlie a portion of the central bending portion 106. The tabs 114, 114' are secured to the lower strip 108 by lugs 118, 118'. The lugs 118, 118' are formed as extentions on the upper strips 110, 110' and are crimped or bent around the portion of the lower strip 108 adjacent the central bending portion 106 as illustrated in FIG. 4.

Constructed from a portion of the lower strip 108 at each end of the arms 104, 104' adjacent loops 112, 112' are downward projecting prongs 120, 120' which terminate at skin piercing points 122, 122'. The prongs 120, 120' are arranged in a converging relationship to facilitate the piercing of the body tissue by the points 122, 122' upon the bending of the suture clip 100 into a clamping position. As illustrated in FIG. 4, the lower strip 108 of the body 102 includes portions 124, 124' which define openings 126, 126' and at least part of the prongs 120, 120', as to be described hereinafter.

Figure 4:
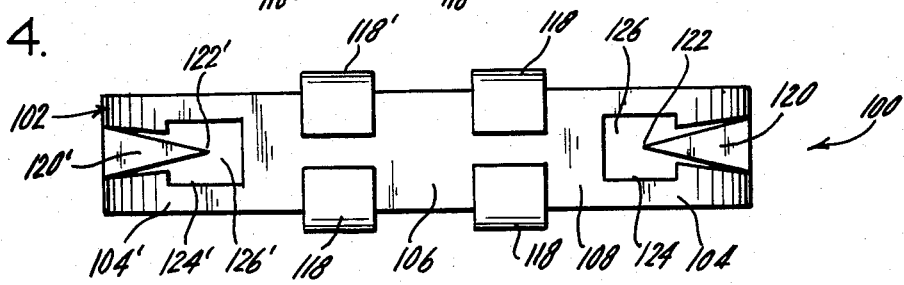
FIG. 4 is a bottom elevation of the one-piece suture clip, as illustrated in FIG. 1.

Referring to FIGS. 1 and 4, the fabrication of one embodiment of a suture clip 100 will now be described. An annealed metal strip having the appropriate dimensions, is passed through a stamping operation using a progressive dye which forms the structural features of the suture clip 100 as previously described. During the stamping operation, the prongs 120, 120' are formed from the metal strip by a cross-cut technique which also forms the points 122, 122'. A first cut removes those areas of the metal strip to provide a protion of the openings 126, 126' and to also define part of the outline of the prongs 120, 120' and portions 124, 124'. A second cut removes those areas of the metal strip to form the complete openings 126, 126', the prongs 120, 120', points 122, 122', and portions 124, 124'. The first and second removed portions overlay in a cross-cut. As seen in FIG. 4, openings 126, 126' are substantially square. The reinforcing webs 116, 116' are formed from the metal strip as a projection punched out during the stamping operation.

The metal strip is fabricated into the shape illustrated in FIG. 1 by appropriately bending the metal strip to form the coacting arms 104, 104', the upwardly extending tabs 114, 114', the downwardly projecting prongs 120, 120', and the lugs 118, 118' crimped adjacent the central bending portion 106.

Figure 2:
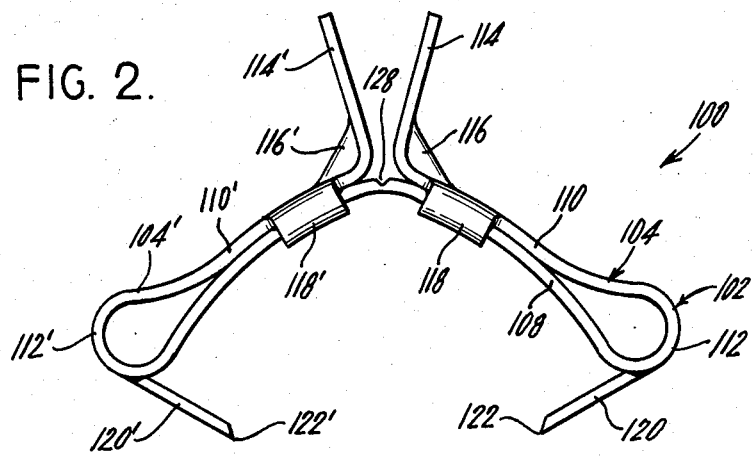
FIG. 2 is a side elevation of the one-piece suture clip, as illustrated in FIG. 1, in a clamping position showing the tabs assuming a substantial V-shaped relationship with the coating arms bent within the bending portion.
Figure 3:
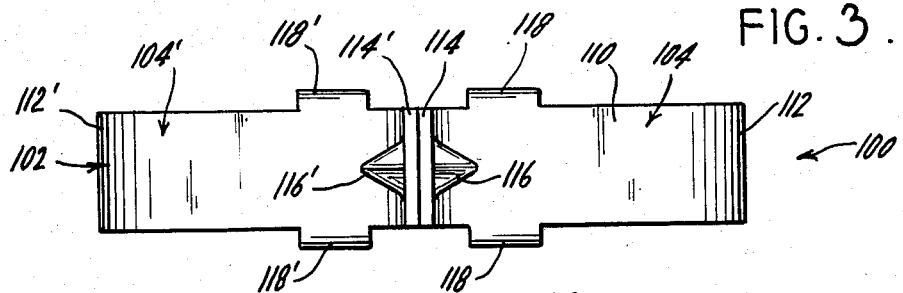
FIG. 3 is a top elevation of the one-piece suture clip, as illustrated in FIG. 1.

The use of the suture clip 100 is now described with reference to FIGS. 1 and 2. The suture clip 100 is provided to the surgeon initially in the shape illustrated in FIG. 1. Once, the suture clip has been bent by the surgeon into the clamping position, it assumes the shape of FIG. 2. In the clamping position, the body 102 has been bent generally within the central bending portion 106. The suture clip 100 may be bent into the clamping position by the surgeon using a suture clip forcep which easily engages the loops 112, 112'. In the clamping position, tabs 114, 114' assume a substantially V-shaped relationship. When the surgeon desires to remove the suture clip 100, the tabs 114, 114' are squeezed together until the pressure on them is sufficient to open and unbend the coacting arms 104, 104'. This opening operation may be done progressing in a series of stages over a period of time to facilitate proper healing. The reinforcing webs 116, 116' provide the tabs 114, 114' with sufficient mechanical strength to allow the force exerted on the tabs to unbend the suture clip 100. When the prongs 120, 120' are fully opened they may be retracted from the body tissue.

The suture clip 100 is constructed from a metal strip having a pre-selected tensile strength such that the force required to bend the suture clip will be acceptable to the operating surgeon. In accordance with another embodiment of the present invention, to compensate for variations in the tensile strength that may occur between metal strips, a groove 128 is formed in the central bending portion 106. The groove 128 is constructed to have suitable dimensions of width and depth in accordance with the tensile strength of the material to provide the suture clip 100 with a pre-selected bending force to cause the suture clip to assume the clamping position. The greater the dimensions of the groove 128, the smaller the bending force required to bend the suture clip 100. The groove 128 is formed in the central bending portion 106 by an approximately sized V-shaped projection on the dye used in the stamping operation to form the suture clip 100. Accordingly, the bending force required to utilize suture clip 100 can be made substantially independent of variations in the tensile strength between metal strips.

Although the invention herein has been described with reference to particular embodiments, it is to be understood that these embodiments are merely illustrative of the principles and application of this invention. Thus, it is to be understood that numerous modifications may be made in the illustrative embodiments and other arrangements may be devised without departing from the spirit and scope of the present invention as defined by the appended claims.

What is claimed is:

1. A one-piece suture clip for holding the edges of a wound proximate to one another comprising, a continuous metal strip formed to include an arched body portion having a pair of co-acting arms, said co-acting arms including a common lower strip having a central bending portion and upper strips bent over the lower strip in overlying relationship to form loops at the opposite ends of said arms, a pair of upwardly extending tabs formed from the free ends of the upper strips overlying the central bending portion, each tab having a first upwardly extending surface in a plane of contact with an essentially parallel first upwardly extending surface of the other tab, wherein said plane of contact is directly overlying the apex of said central bending portion:

said central bending portion defining a groove or variable width and depth, the dimensions thereof in accordance with variations in the tensile strength of said metal strip so that the relationship between the tensile strength and the dimensions of said groove results in a constant force being required to bend the suture clip and so that the bending force required to utilize a plurality of suture clips is independent of variations in the tensile strength between metal strips;

reinforcing webs integrally formed between second upwardly extending surfaces of said upwardly extending tabs and the upper strips and overlying a portion of the central bending portion, said upwardly extending tabs and said strips being secured to the lower strips by lugs integrally formed with and as extensions on said upper strips and secured around a portion of the lower strips adjacent the bending portion; and downwardly projecting prongs terminating in skin piercing points integrally formed from a portion of the lower strip at opposite ends of the arms by removing portions of the lower metal strip leaving substantially square openings therein and arranged in converging relationship to facilitate the piercing of the body tissue by the points upon bending of the suture clip into a clamping position.

2. The suture clip of claim 1, wherein said groove is V-shaped.

3. The suture clip of claim 1, wherein said metal strip is composed of an alloy comprising copper, nickel and zinc.

* * * * *